United States Patent
Ando

(10) Patent No.: US 10,358,530 B2
(45) Date of Patent: Jul. 23, 2019

(54) POLYETHER-MODIFIED SILOXANE AND A THICKENING AGENT

(71) Applicant: Shin-Etsu Chemical Co., Ltd., Tokyo (JP)

(72) Inventor: Yuji Ando, Annaka (JP)

(73) Assignee: SHIN-ETSU CHEMICAL CO., LTD., Tokyo (JP)

(*) Notice: Subject to any disclaimer, the term of this patent is extended or adjusted under 35 U.S.C. 154(b) by 0 days.

(21) Appl. No.: 15/797,560

(22) Filed: Oct. 30, 2017

(65) Prior Publication Data

US 2018/0118891 A1 May 3, 2018

(30) Foreign Application Priority Data

Oct. 31, 2016 (JP) .................. 2016-213241

(51) Int. Cl.
- C08G 77/46 (2006.01)
- A61K 8/894 (2006.01)
- A61Q 5/02 (2006.01)
- A61Q 5/12 (2006.01)
- C08L 83/04 (2006.01)
- C08G 77/14 (2006.01)

(52) U.S. Cl.
CPC .............. *C08G 77/46* (2013.01); *A61K 8/894* (2013.01); *A61Q 5/02* (2013.01); *A61Q 5/12* (2013.01); *C08L 83/04* (2013.01); *A61K 2800/48* (2013.01); *C08G 77/14* (2013.01)

(58) Field of Classification Search
None
See application file for complete search history.

(56) References Cited

U.S. PATENT DOCUMENTS 8,912,354 B2 * 12/2014 Kamei .................. A61K 8/06
556/432

FOREIGN PATENT DOCUMENTS

JP 4825849 B2 11/2011

OTHER PUBLICATIONS

Kao et al, Biomacromolecules 2003, 4, 1055-1067.*

* cited by examiner

*Primary Examiner* — Clinton A Brooks
(74) *Attorney, Agent, or Firm* — Birch, Stewart, Kolasch & Birch, LLP

(57) ABSTRACT

One of the purposes of the present invention is to provide a polyether-modified siloxane having a good thickening property, in particular a good thickening property for an aqueous liquid. The present invention provides a polyether-modified siloxane represented by the following general formula (1):

$$Sx\text{-}(CH_2)_aCOO\text{---}(C_2H_4O)_n\text{---}(C_3H_6O)_s\text{---}CO(CH_2)_a\text{-}Sx \quad (1)$$

wherein n is an integer of from 50 to 10000, s is an integer which meets the equation, $0 \leq s \leq n/50$, a is an integer of from 2 to 40, and Sx is, independently of each other, an organo(poly)siloxanyl group represented by the following formula (a) or (b):

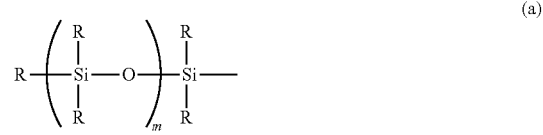

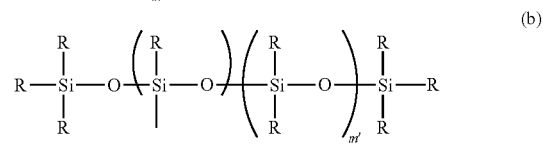

wherein R is, independently of each other, a hydrogen atom, a hydroxyl group, an alkoxyl group, or a substituted or unsubstituted monovalent hydrocarbon group having 1 to 20 carbon atoms, m is an integer of from 0 to 350, and m' is an integer of from 0 to 348, wherein a ratio of a total molecular weight of the $Sx\text{-}(CH_2)_a CO$ moieties to a molecular weight of the $O(C_2H_4O)_n(C_3H_6O)_s$ moiety is 0.12 or smaller.

7 Claims, No Drawings

POLYETHER-MODIFIED SILOXANE AND A THICKENING AGENT

CROSS REFERENCE

This application claims the benefits of Japanese Patent Application No. 2016-213241 filed on Oct. 31, 2016, the contents of which are hereby incorporated by reference.

FIELD OF THE INVENTION

The present invention relates to a polyether-modified siloxane having a good thickening property, a method for preparing the same and a thickening agent comprising the polyether modified siloxane, in particular a thickening agent for an aqueous liquid.

Many types of thickening agents for aqueous liquids are known in various fields such as cosmetics and household. Examples of them are natural polymers such as a corn starch and pectin, semi-synthetic polymers such as carboxymethyl cellulose, and oxidized starch, and synthetic polymers such as sodium polyacrylate and polyethylene oxide.

Compounds having hydrophobic groups at both terminals of polyethylene glycol are also known as a thickening agent. For instance, Patent Literature 1 descries a compound having siloxane groups at both terminals of polyethylene glycol. Patent literature 1 describes a method for preparing the compound, using hexamethylene diisocyanate or adipic acid. However, when hexamethylene diisocyanate is used, a product is formed by alternative reaction of hexamethylene diisocyanate and polyethylene glycol and, therefore, a molecular weight of the product cannot be controlled. This problem occurs also in a method using adipic acid.

Further, Patent Literature 1 also describes a product obtained by reacting a siloxane having an epoxy group at one terminal with a polyethylene glycol. Although the molecular weight of the product can be controlled in this reaction, the reactivity between the siloxane having an epoxy group at one terminal and the polyethylene glycol is low. Therefore, there is such a problem that a large amount of the raw materials remain unreacted. The function of the compound obtained in this method is insufficient as a thickening agent.

PRIOR LITERATURES

Patent Literature 1: Japanese Patent No. 4825849

SUMMARY OF THE INVENTION

One of the purposes of the present invention is to provide a polyether-modified siloxane having a good thickening property, in particular a good thickening property for an aqueous liquid.

The present inventors have made research and found that a molecular weight of the polyether-modified siloxane can be controlled by bonding a siloxane and a polyalkylene glycol together via an ester bond. Further, the present inventors have found that a good thickening property is provided on account of a specific ratio of a molecular weight of the siloxane moiety to a molecular weight of the polyoxyalkylene moiety in the polyether-modified siloxane.

Thus, the present invention provides a polyether-modified siloxane represented by the following general formula (1):

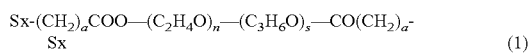

$$\text{Sx-(CH}_2)_a\text{COO—(C}_2\text{H}_4\text{O})_n\text{—(C}_3\text{H}_6\text{O})_s\text{—CO(CH}_2)_a\text{-Sx} \quad (1)$$

wherein n is an integer of from 50 to 10000, s is an integer which meets the equation, $0 \leq s \leq n/50$, a is an integer of from 2 to 40, and Sx is, independently of each other, an organo(poly)siloxanyl group represented by the following formula (a) or (b):

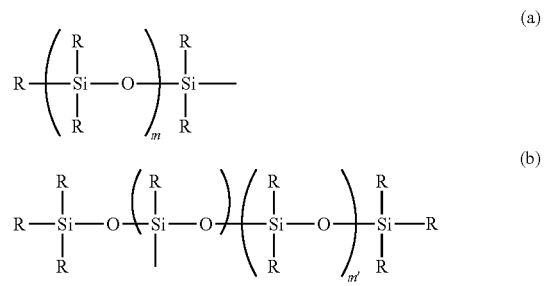

wherein R is, independently of each other, a hydrogen atom, a hydroxyl group, an alkoxyl group, or a substituted or unsubstituted monovalent hydrocarbon group having 1 to 20 carbon atoms, m is an integer of from 0 to 350, and m' is an integer of from 0 to 348, wherein a ratio of a total molecular weight of the Sx-$(CH_2)_a$CO moieties to a molecular weight of the O$(C_2H_4O)_n$$(C_3H_6O)_s$ moiety is 0.12 or smaller.

Further, the present invention provides a thickening agent comprising the aforesaid polyether-modified siloxane, particularly a thickening agent for an aqueous liquid.

Effects of the Invention

The present polyether-modified siloxane has a good thickening property, in particular in an aqueous liquid. Accordingly, the present polyether-modified siloxane functions as a thickening agent in various fields such as cosmetics, households, additives for coating materials and fiber treating agents. In particular, the polyether-modified siloxane is usable as a thickening agent for cosmetics and household products such as hair-care products, e.g., shampoos and hair conditioners.

DETAILED DESCRIPTION OF THE INVENTION

The present invention is the polyether-modified siloxane which is represented by the aforesaid general formula (1) and characterized in that the ratio of the total molecular weight of the Sx-$(CH_2)_a$CO moieties to the molecular weight of the O$(C_2H_4O)_n$$(C_3H_6O)_s$ moiety is 0.12 or smaller. On account of this ratio, the polyether-modified siloxane has a good thickening property, in particular in an aqueous liquid. The ratio is preferably 0.11 or smaller. If the molecular ratio is larger than the aforesaid upper limit, the polyether-modified siloxane hardly dissolves in water and its thickening property, particularly in an aqueous liquid, becomes poor. Further, the siloxane moieties and the polyoxyalkylene moiety are bonded via an ester bond in the present polyether-modified siloxane and, therefore, the molecular weight is easily controlled according to the method described below. Therefore, the compound having a desired molecular weight is provided with a good yield.

In the formula (1), R is a hydrogen atom, a hydroxyl group, an alkoxyl group, or a substituted or unsubstituted monovalent hydrocarbon group having 1 to 20 carbon atoms. Examples of a monovalent hydrocarbon group having 1 to 20 carbon atoms include an alkyl group having 1 to 20 carbon atoms, a cycloalkyl group having 3 to 20 carbon atoms, an alkenyl group having 2 to 20 carbon atoms, an aryl group having 6 to 20 carbon atoms and an aralkyl group having 7 to 20 carbon atoms. Specifically, examples of the unsubstituted monovalent hydrocarbon group include an alkyl group such as a methyl group, an ethyl group, a propyl group, a butyl group, a pentyl group, a hexyl group, a heptyl group, an octyl group, a nonyl group, a decyl group, a dodecyl group, a tetradecyl group, a hexadecyl group and an octadecyl group; a cycloalkyl group such as a cyclopentyl group and a cyclohexyl group; an alkenyl group such as a vinyl group and an allyl group; an aryl group such as a phenyl group, a tolyl group and a naphthyl group; and an aralkyl group such as a benzyl group and a phenethyl group. Examples of the substituted monovalent hydrocarbon group include groups such as those hydrocarbon groups wherein a part or all of the hydrogen atoms bonded to a carbon atom of the aforesaid groups is substituted with a substituent such as a halogen atom, an amino group, an acryloxy group, a methacryloxy group, an epoxy group, a mercapto group, a carboxyl group and a hydroxyl group.

R is preferably a hydrocarbon group having 1 to 6 carbon atoms such as a methyl group, an ethyl group, a propyl group, a butyl group and a phenyl group, further preferably a methyl group, a butyl group and a phenyl group.

In the aforesaid compound represented by the formula (1), the structure represented by ($C_3H_6O$) may have a branch. Specifically, ($C_3H_6O$) is preferably one of the following structures.

($CH_2CH_2CH_2O$)

(CMeHCH$_2$O)

($CH_2$CMeHO)

The ($C_2H_4O$) and ($C_3H_6O$) units may form a block or bond randomly in the formula (1).

m is an integer of from 0 to 350, preferably 1 to 150, further preferably 2 to 80. m' is an integer of from 0 to 348, preferably 0 to 148 and further preferably 0 to 78. n is an integer of from 50 to 10000, preferably 80 to 5000, further preferably 100 to 1000. s is an integer which meets the equation, $0 \leq s \leq n/50$.

a is an integer of from 2 to 40, preferably 2 to 20, further preferably 2 to 15.

The method for preparing the aforesaid polyether-modified siloxane is, for instance, the following methods 1 to 3.

Method 1: a dehydration-condensation reaction of a siloxane having one carboxyl group with a polyoxyalkylene.

Method 2: a dealcoholization-condensation reaction of a siloxane having one ester group with a polyoxyalkylene.

Method 3: a hydrosilylation of a siloxane having one SiH group with a compound obtained by a dehydration-condensation or dealcoholization-condensation of a polyoxyalkylene with a carboxylic acid or its ester which has a carbon-carbon double-bond at the terminal.

The each method will be explained below in detail.
1: Preparation by a Dehydration-Condensation Reaction The siloxane having one carboxyl group is represented, for instance, by the following formula (2a) or (2b).

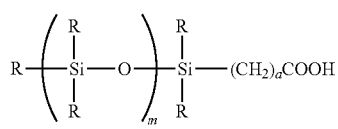

(2a)

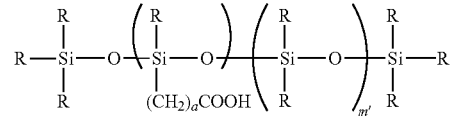

wherein R, a, m and m' are as defined above.

The polyoxyalkylene is represented, for instance, by the following formula (3).

$$HO-(C_2H_4O)_n(C_3H_6O)_s-H \quad (3)$$

wherein n and s are as defined above, ($C_3H_6O$) may have a branch, and ($C_2H_4O$) and ($C_3H_6O$) units may form a block or bond randomly.

The dehydration-condensation reaction of a siloxane having a carboxyl group with a polyoxyalkylene may be conducted in any known manner, such as Fischer esterification or a method using dehydration-condensation agent. Further, an esterification using a halogenated sulfonyl may be adopted. This esterification is preferable because it has high reactivity and a molecular weight of the polyether-modified siloxane obtained is easily controlled.

In Fischer esterification, generally, a carboxylic acid and an alcohol are subjected to dehydration-condensation in the presence of an acid catalyst such as sulfuric acid and para-toluenesulfonic acid. The reaction is of equilibration and it is necessary to remove the formed water from the reaction system. For this end, use may be made of azeotropic distillation with benzene or toluene in a Dean-Stark apparatus. Alternatively, the water may be removed by adding a dehydrating agent, such as anhydrous magnesium sulfate and molecular sieve, in a Soxhlet extractor and by refluxing a solvent.

Examples of the dehydration-condensation agent include dicyclohexylcarbodiimide, 1,1-carbonyldiimidazole and bis(2-oxo-3-oxazolidinyl)phosphinic chloride. An additive, such as 4-(dimethylamino)pyridine, may be added. The siloxane having a carboxyl group, the polyoxyalkylenesioxane, the dehydration-condensation agent and, if needed, the additive are mixed in the presence of a solvent such as dichloromethane and allowed to react.

The esterification using a halogenated sulfonyl comprises, specifically, a step of reacting a siloxane having a carboxyl group with a halogenated sulfonyl and further a step of reacting the obtained reaction product with a polyoxyalkylene to thereby obtain a polyether-modified siloxane represented by the aforesaid formula (1). These steps both are preferably carried out in the presence of an amine. In this method, the siloxane bonds are not broken, so that a polyether-modified siloxane having a desired molecular weight can be obtained with a high yield.

The halogenated sulfonyl is represented by the general formula: R'—SO$_2$—X. R' is a monovalent hydrocarbon group having 1 to 20 carbon atoms, such as an alkyl, aryl, or dialkylamino group, preferably a methyl group, a phenyl group, an o-tolyl group, a m-tolyl group, a p-tolyl group, a xylyl group, a mesityl group, and a Me$_2$N— group, in particular, a p-tolyl group and a Me$_2$N— group. X is a halogen atom such as fluorine, chlorine, bromine and iodine atoms. A chlorine atom is preferable.

Amine is, for instance, aliphatic amines such as trimethylamine, dimethylbutylamine, 1-propylamine, 2-propylamine, n-butylamine, t-butylamine, cyclopentylamine and cyclohexylamine; heterocyclic amines such as piperidine, piperazine, morpholine, quinuclidine, 1,4-diazabicyclo

[2.2.2]octane (DABCO), pyrrole, pyrazole, imidazole, 1-methylimidazole, pyridine, pyridazine, pyrimidine, pyrazine, oxazole, thiazole, and 4-dimetylaminopyridine. Preferred are trimethylamine, dimethylbutylamine, 4-dimetylaminopyridine, pyridine, imidazole, and 1-methylimidazole, further preferably trimethylamine, dimethylbutylamine, 4-dimetylaminopyridine, pyridine, and 1-methylimidazole.

The method using halogenated sulfonium may be conducted in the presence of a reaction solvent. Any solvent may be used such as toluene, xylene, benzene, hexane, cyclohexane, methylcyclohexane, ethylcyclohexane, chloroform, dichloromethane, carbon tetrachloride, THF, diethylether, acetone, methylethyl ketone, DMF, and acetonitrile. Preferred are toluene, xylene and acetonitrile.

The reaction process will be described below in detail. First, a siloxane having a carboxyl group, a halogenated sulfonium and a reaction solvent are stirred, and allowed to react at a temperature of 0 to 200 degrees C., preferably 10 to 100 degrees C., particularly 15 to 50 degrees, for at most 5 hours, preferably for at most 3 hours. Thereafter, polyoxyalkylene is added and stirred, and allowed to react at a temperature of 0 to 200 degrees C., preferably 10 to 150 degrees C., particularly 15 to 100 degrees, for at most 24 hours, preferably for at most 10 hours.

2: Preparation by Dealcoholization-Condensation

A siloxane having one ester group is represented, for instance, by the following formula (2c) or (2d).

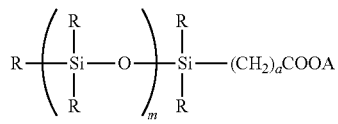
(2c)

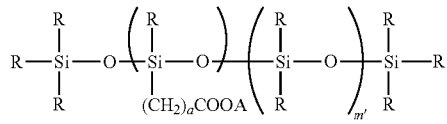
(2d)

wherein R, a, m and m' are as defined above.

In the formula (2c) and (2d), A is, for instance, an alkyl group such as a methyl group, an ethyl group and a butyl group or an aryl group such as a phenyl group, an o-tolyl group, a m-tolyl group, a p-tolyl group, a xylyl group, a mesityl group and a naphthyl group.

Polyoxyalkylene is represented, for instance, by the aforesaid formula (3).

The dealcoholization-condensation of the carboxylic acid-containing siloxane with a polyoxyalkylene may be carried out in any known manner. For instance, it may be carried out using a catalyst such as an acid, e.g., Bronsted acid and Lewis acid, or a base. The reaction proceeds with removing a formed alcohol from the reaction system.

3: Preparation by a Hydrosilylation

The carboxylic acid having a carbon-carbon double-bond at the terminal is represented, for instance, by $H_2C=CH(CH)_aCOOH$. The ester of this acid is represented by $H_2C=CH(CH)_aCOOA$. a' is a value of "a minus 2". A is, for instance, an alkyl group such as a methyl group, an ethyl group and a butyl group or an aryl group such as a phenyl group, an o-tolyl group, a m-tolyl group, a p-tolyl group, a xylyl group, a mesityl group and a naphthyl group. Polyoxyalkylene is represented, for instance, by the aforesaid formula (3).

The dehydration-condensation or dealcoholization-condensation of the carboxylic acid or its ester having a carbon-carbon double-bond at the terminal with the polyoxyalkylene may be conducted according to the aforesaid method 1 or 2 to thereby obtain the compound represented by the following formula.

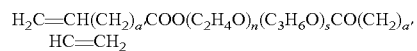

wherein a', a, n and s are as defined above. This compound is hydrosilylated with a siloxane having one SiH group in the molecular to thereby obtain the compound represented by the aforesaid formula (1).

The siloxane having one SiR group in the molecular is represented, for instance, by the following formula (2e) or (2f).

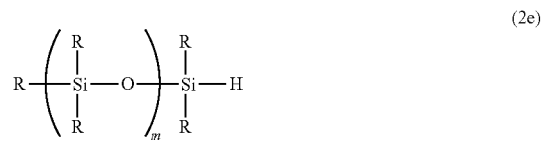
(2e)

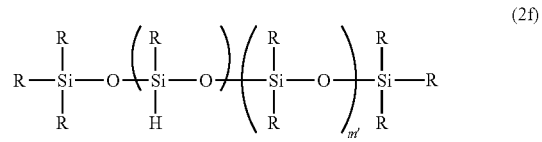
(2f)

wherein R, m and m' are as defined above.

The hydrosilylation may be carried out in any known manner. For example, the hydrosilylation may be carried out in the presence of a catalyst such as a metal catalyst having platinum, palladium, rhodium, ruthenium, gold or nickel. Particularly, a catalyst having platinum, palladium or rhodium is preferred. A catalyst having platinum is more preferably. Specifically, $PtCl_4$, $H_2PtCl_6.6H_2O$, Pt-ether complex, Pt-olefin complex, $PdCl_2(PPh_3)_2$, $PdCl_2(PhCN)_2$, and $RhCl_2(PPh_3)_3$ can be used, wherein Ph is a phenyl group. These catalysts may be used alone or in combination of two or more of them. If needed, the catalyst may be diluted with a solvent such as alcohols, aromatic compounds, hydrocarbons, ketones and basic solvents. In particular, a complex of 1,1,3,3-tetramethyl-1,3-divinyldisiloxane and a chloroplatinic acid neutralized with sodium bicarbonate (i.e., Karstedt's catalyst) is most suitable as a hydrosilylation catalyst.

The hydrosilylation may be conducted in the presence of a solvent, such as toluene, xylene, benzene, hexane, cyclohexane, methylcyclohexane, ethylcyclohexane, chloroform, dichloromethane, carbon tetrachloride, THF, diethyl ether, acetone, methyl ethyl ketone, DMF, acetonitrile, methanol, ethanol, 1-propanol, 2-propanol, 1-butanol and 2-butanol.

The temperature of the hydrosilylation may be as in known manners, generally 20 to 250 degrees C., preferably 40 to 180 degrees C., particularly 80 to 120 degrees C. The reaction time is for at most 20 hours, preferably for at most 12 hours, particularly for at most 8 hours.

As described above, the polyoxyalkylene modified siloxane of the present invention has an excellent thickening property, particularly an excellent thickening property for water. Therefore, the polyoxyalkylene modified siloxane functions suitably as a thickening agent for an aqueous liquid. In the present specification, the aqueous liquid includes, for example, an aqueous solution in which a water-soluble substance is completely dissolved in water and an aqueous dispersion in which a water-insoluble substance is dispersed in water. For instance, the polyoxyalkylene modified siloxane functions suitably as a thickening agent in aqueous cosmetics, aqueous household products, aqueous paints, aqueous fiber treatment agents and aqueous hair care products such as shampoos and rinses. In particular, it is a thickening agent to be added to aqueous cosmetics, aqueous hair care products and aqueous household products.

The polyoxyalkylene modified siloxane as a thickening agent may be used like known thickening agents. The amount of the thickening agent may be properly selected depending on the kinds of liquids, and is not limited. For instance, the amount of the thickening agent is 0.5 to 50% by mass, relative to a mass of the aqueous solution. When the thickening agent is added in the aforesaid amount, water is well thickened. Alternatively, the amount of the thickening agent in the aqueous solution or dispersion is preferably 0.5 to 50% by mass, relative to a total mass of water and the thickening agent.

EXAMPLES

The present invention will be explained below in further detail with reference to a series of the Examples and the Comparative Examples, though the present invention is in no way limited by these Examples.

Carboxy group-containing siloxanes A to G used in the Examples or the Comparative Examples are as follows.

Carboxy Group-Containing Siloxane A:
  $Me_3SiOSiMe_2$-$(CH_2)_{10}COOH$, Molecular weight: 333

Carboxy Group-Containing Siloxane B:
  $(Me_3SiO)_2MeSi$—$(CH_2)_{10}COOH$, Molecular weight: 407

Carboxy Group-Containing Siloxane C:
  $BuMe_2Si(OSiMe_2)_4$-$(CH_2)_{10}COOH$, Molecular weight: 597

Carboxy Group-Containing Siloxane D:
  $BuMe_2Si(OSiMe_2)_9$-$(CH_2)_{10}COOH$, Molecular weight: 968

Carboxy Group-Containing Siloxane E:
  $BuMe_2Si(OSiMe_2)_{16}$-$(CH_2)_{10}COOH$, Molecular weight: 1487

Carboxy Group-Containing Siloxane F:
  $BuMe_2Si(OSiMe_2)_{31}$-$(CH_2)_{10}COOH$, Molecular weight: 2599

Carboxy Group-Containing Siloxane G:
  $BuMe_2Si(OSiMe_2)_{61}$-$(CH_2)_{10}COOH$, Molecular weight: 4824

Example 1a 3.5 Mole equivalents of carboxy group-containing siloxane A, 3.5 mole equivalents of p-toluenesulfonyl chloride and 10.5 mole equivalents of 1-methylimidazole were mixed in a toluene solvent at room temperature for 30 minutes to which 1.0 mole equivalent of PEG 6000 (average molecular weight: 6000) was then added and allowed to react at 80 degrees C. for 20 hours. Then, toluene was distilled off at 80 degrees C./10 mmHg. A resulting solid was well crushed, to which ethanol was added and stirred for one hour. Then, the solid was filtered off and washed with ethanol to remove the unreacted raw materials. Finally, ethanol was distilled off at 30 degrees C./10 mmHg with a reduced-pressure drier to obtain a white solid product. The product obtained was analyzed by GPC and a monomodal peak was confirmed. The compound obtained had the following structure:

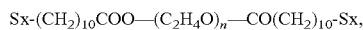

wherein Sx was $Me_3SiOSiMe_2$-, n was the number such that the average molecular weight of HO—$(C_2H_4O)_n$—H was 6000, which is called PEG6000.

Comparative Example 1a to 1f

The procedures of Example 1a were repeated to obtain a white solid product, except that carboxy group-containing siloxane B, C, D, E, F or G was used instead of carboxy group-containing siloxane A used in Example 1a.

Example 2a

The procedures of Example 1a were repeated to obtain a white solid product, except that PEG20000 (average molecular weight: 20000) was used instead of PEG6000 (average molecular weight: 6000) used in Example 1a.

Examples 2b to 2d

The procedures of Example 2a were repeated to obtain a white solid product, except that carboxy group-containing siloxane B, C or D was used instead of carboxy group containing siloxane A used in Example 2a.

Comparative Examples 2a to 2c

The procedures of Example 2a were repeated to obtain a white solid product, except that carboxy group-containing siloxane E, F or G was used instead of carboxy group-containing siloxane A used in Example 2a.

Example 3a

The procedures of Example 1a were repeated to obtain a white solid product, except that PEG40000 (average molecular weight: 40000) was used instead of PEG6000 (average molecular weight: 6000) used in Example 1a.

Examples 3b to 3e

The procedures of Example 3a were repeated to obtain a white solid product, except that carboxy group-containing siloxane B, C, D or E was used instead of carboxy group-containing siloxane A used in Example 3a.

Comparative Examples 3a and 3b

The procedures of Example 3a were repeated to obtain a white solid product, except that carboxy group-containing siloxane F or G was used instead of carboxy group-containing siloxane A used in Example 3a.

The compounds obtained in the aforesaid Examples and Comparative Examples are represented by the following structure:

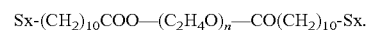

n is the number such that an average molecular weight of HO—$(C_2H_4O)_n$—H is 6000, 20,000, or 40,000, each being called "PEG 6000", "PEG 20000", or "PEG 40000".

Sx is a residue derived from any one of carboxy group-containing siloxanes A to G. For instance, Sx is $Me_3SiOSiMe_2$- in the compound which was prepared using carboxy group-containing siloxane A as a raw material.

The ratio of [total molecular weight of the Sx-$(CH_2)_{10}CO$ moieties]/[molecular weight of the $O(C_2H_4O)_n$ moiety] in the compound obtained in the Example or the Comparative Example is as shown in the Tables 1 and 2.

Thickening Test

The thickening property of the polyether-modified siloxane obtained in the aforesaid Examples and the Comparative Examples were evaluated according to the following manner.

5 Grams of the polyether-modified siloxane and 95 grams of water were put in a 100-milliliter glass bottle and mixed for 3 hours with a shaking apparatus. The behavior was visually observed to see how a viscosity of the mixture increased. The results were rated according to the following criteria and shown in Tables 1 and 2.

A: The viscosity of the mixture increased very much.
B: The viscosity of the mixture increased slightly.
C: The viscosity of the mixture did not increase.

TABLE 1

| | Molecular weight of $Sx-(CH_2)_{10}CO$ | Molecular weight of $O(C_2H_4O)_n$ | Ratio of the molecular weights | Thickening property |
|---|---|---|---|---|
| Example 1a | 632 | 5998 | 0.105 | A |
| Example 2a | 632 | 19998 | 0.032 | A |
| Example 2b | 780 | | 0.039 | A |
| Example 2c | 1160 | | 0.058 | A |
| Example 2d | 1902 | | 0.095 | A |
| Example 3a | 632 | 39998 | 0.016 | A |
| Example 3b | 780 | | 0.020 | A |
| Example 3c | 1160 | | 0.029 | A |
| Example 3d | 1902 | | 0.048 | A |
| Example 3e | 2940 | | 0.074 | A |

TABLE 2

| | Molecular weight of $Sx-(CH_2)_{10}CO$ | Molecular weight of $O(C_2H_4O)_n$ | Ratio of the molecular weight | Thickening property |
|---|---|---|---|---|
| Comparative Example 1a | 780 | 5998 | 0.13 | C |
| Comparative Example 1b | 1160 | | 0.19 | C |
| Comparative Example 1c | 1902 | | 0.32 | C |
| Comparative Example 1d | 2940 | | 0.49 | C |
| Comparative Example 1e | 5164 | | 0.86 | C |
| Comparative Example 1f | 9614 | | 1.6 | C |
| Comparative Example 2a | 2940 | 19998 | 0.15 | B |
| Comparative Example 2b | 5164 | | 0.26 | C |
| Comparative Example 2c | 9614 | | 0.48 | C |
| Comparative Example 3a | 5164 | 39998 | 0.13 | B |
| Comparative Example 3b | 9614 | | 0.24 | C |

As shown in Tables 1 and 2, the present polyether-modified siloxane which has the specific ratio of the total molecular weight of the siloxane moieties to the molecular weight of the oxyalkylene moiety has the good thickening property. In contrast, as shown in the Comparative Examples, the polyether-modified siloxane having the ratio of larger than 0.12 has the poor thickening property.

Comparative Example 4

1.0 Mole equivalent of PEG20000 (molecular weight: 20000), 2.0 mole equivalents of $BuMe_2Si(OSiMe_2)_9$-$C_3H_6OC_2H_4OH$, 2.08 mole equivalents of hexamethylene isocyanate, 0.024 mole equivalent of dibutyltin dilaurate and toluene were mixed and heated at 80 degrees C. for 8 hours. Then, toluene was distilled off at 80 degrees C./10 mmHg. A resulting solid was well crushed, to which ethanol was added and stirred for one hour. Then, the solid was filtered off and washed with ethanol to remove the unreacted raw materials. Finally, ethanol was distilled off at 30 degrees C./10 mmHg with a reduced-pressure drier to obtain a white solid product. A peak confirmed by GPC analysis was multiplet and, therefore, the desired compound could not be obtained.

Comparative Example 5

1.0 Mole equivalent of PEG20000 (molecular weight: 20000), 3.0 mole equivalents of compound which has an epoxy group and represented by the following general formula:

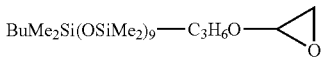

0.63 mole equivalent of potassium laurate were mixed in a toluene solvent and heated at 110 degrees C. for 24 hours. Then, toluene was distilled off at 80 degrees C./10 mmHg. A resulting solid was well crushed, to which ethanol was added and stirred for one hour. Then, the solid was filtered off and washed with ethanol to remove the unreacted raw materials. Finally, ethanol was distilled off at 30 degrees C./10 mmHg with a reduced-pressure drier to obtain a white solid product. Few peaks of the siloxane were confirmed by $^1$H-NMR. This means that the siloxane did not react.

The present polyether-modified siloxane has good thickening property. Therefore, the present polyether-modified siloxane is usable as a thickening agent for cosmetics and household products such as hair-care products, e.g., shampoos and hair conditioners.

The invention claimed is:

1. A polyether-modified siloxane represented by the following general formula (1):

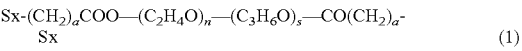

wherein n is an integer of from 50 to 10000, s is an integer which meets the equation, $0 \leq s \leq n/50$, a is an integer of from 2 to 40, and Sx is, independently of each other, an organo(poly)siloxanyl group represented by the following formula (a) or (b):

-continued

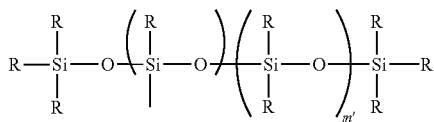
(b)

wherein R is, independently of each other, a hydrogen atom, a hydroxyl group, an alkoxyl group, or a substituted or unsubstituted monovalent hydrocarbon group having 1 to 20 carbon atoms, m is an integer of from 1 to 350, and m' is an integer of from 0 to 348, wherein a ratio of a total molecular weight of the $Sx$-$(CH_2)_aCO$ moieties to a molecular weight of the $O(C_2H_4O)_n(C_3H_6O)_s$ moiety is 0.12 or smaller.

2. A thickening agent comprising the polyether-modified siloxane according to claim 1.

3. A method for thickening an aqueous liquid by mixing the thickening agent according to claim 2 and the aqueous liquid.

4. An aqueous solution comprising the thickening agent according to claim 2, wherein an amount of the thickening agent is 0.5 to 50 mass %, based on a total mass of water and the thickening agent.

5. An aqueous dispersion comprising the thickening agent according to claim 2, wherein an amount of the thickening agent is 0.5 to 50 mass %, based on a total mass of water and the thickening agent.

6. A method for preparing the polyether-modified siloxane according to claim 1, wherein the method comprises a step of reacting $Sx$-$(CH_2)_aCOOH$ with a halogenated sulfonyl compound and a step of reacting the compound obtained in the aforesaid step with $HO(C_2H_4O)_n$—$(C_3H_6O)_sH$ to thereby obtain the polyether-modified siloxane.

7. The method according to claim 6, wherein the halogenated sulfonyl compound is R'—$SO_2$—X, wherein R' is an alkyl group, an aryl group or a dialkylamino group and X is a halogen atom.

* * * * *